(12) United States Patent
Chinnayelka et al.

(10) Patent No.: US 9,173,597 B2
(45) Date of Patent: Nov. 3, 2015

(54) ANALYTE SENSORS, SYSTEMS, TESTING APPARATUS AND MANUFACTURING METHODS

(75) Inventors: Swetha Chinnayelka, Tarrytown, NY (US); Jiangfeng Fei, Sleepy Hollow, NY (US); Narasinha Parasnis, Nanuet, NY (US); Serban Peteu, East Lansing, MI (US); Yuan Wang, Mountain Lakes, NJ (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 172 days.

(21) Appl. No.: 13/119,222

(22) PCT Filed: Sep. 18, 2009

(86) PCT No.: PCT/US2009/057372
§ 371 (c)(1),
(2), (4) Date: Apr. 7, 2011

(87) PCT Pub. No.: WO2010/033741
PCT Pub. Date: Mar. 25, 2010

(65) Prior Publication Data
US 2011/0180405 A1    Jul. 28, 2011

Related U.S. Application Data

(60) Provisional application No. 61/098,726, filed on Sep. 19, 2008.

(51) Int. Cl.
*G01N 27/327* (2006.01)
*A61B 5/15* (2006.01)
(Continued)

(52) U.S. Cl.
CPC ............ *A61B 5/1411* (2013.01); *A61B 5/14532* (2013.01); *A61B 5/14865* (2013.01);
(Continued)

(58) Field of Classification Search
CPC .................................................. G01N 27/3271
USPC ........................ 204/403.01–403.15; 205/781, 205/783.5–785, 787
See application file for complete search history.

(56) References Cited

U.S. PATENT DOCUMENTS 4,326,927 A    4/1982    Stetter et al.
4,596,741 A    6/1986    Endou et al.
(Continued)

FOREIGN PATENT DOCUMENTS

WO    WO 2006/057722    6/2006
WO    WO 2009/100082    8/2009
(Continued)

OTHER PUBLICATIONS

Isao Karube et al., "Integrated Microbiosensors for Medical Use", Dec. 1, 1989, Annals of New York Academy of Sciences, vol. 542, No. 9, pp. 470-479.
(Continued)

*Primary Examiner* — Bach Dinh
(74) *Attorney, Agent, or Firm* — Dugan & Dugan PC

(57) ABSTRACT

In some aspects, an analyte sensor is provided for detecting an analyte concentration level in a bio-fluid sample. The analyte sensor may include one or more conductors received in a hollow portion of a hollow member. The first conductor may be made, at least in part, of a semiconductor material and an active region may be provided in contact with at least the first conductor. The analyte sensor may, in one aspect, include a lancet and an integrated sensor. Manufacturing methods and apparatus and systems utilizing the analyte sensors are provided, as are numerous other aspects.

18 Claims, 7 Drawing Sheets

(51) Int. Cl.
*A61B 5/145* (2006.01)
*A61B 5/1486* (2006.01)
*A61B 5/151* (2006.01)
*A61B 5/157* (2006.01)

(52) U.S. Cl.
CPC ............... *A61B5/157* (2013.01); *A61B 5/1513* (2013.01); *A61B 5/150022* (2013.01); *A61B 5/15113* (2013.01); *A61B 5/15117* (2013.01); *A61B 5/15123* (2013.01); *A61B 5/15151* (2013.01); *A61B 5/150297* (2013.01); *A61B 5/150389* (2013.01); *A61B 5/150503* (2013.01); *A61B 5/150755* (2013.01); *A61B 5/150786* (2013.01); *A61B 5/15159* (2013.01); *A61B 2562/08* (2013.01); *A61B 2562/085* (2013.01); *Y10T 29/49002* (2015.01)

(56) References Cited

U.S. PATENT DOCUMENTS

| | | | | |
|---|---|---|---|---|
| 5,223,124 | A | * | 6/1993 | Ege .......................... 204/403.09 |
| 5,338,415 | A | | 8/1994 | Sailor et al. |
| 5,431,800 | A | * | 7/1995 | Kirchhoff et al. ........ 204/403.01 |
| 5,476,776 | A | | 12/1995 | Wilkins |
| 5,611,900 | A | | 3/1997 | Worden et al. |
| 5,627,922 | A | | 5/1997 | Kopelman et al. |
| 5,634,913 | A | * | 6/1997 | Stinger ......................... 604/272 |
| 5,700,695 | A | | 12/1997 | Yassinzadeh et al. |
| 5,777,372 | A | | 7/1998 | Kobashi |
| 5,866,353 | A | | 2/1999 | Berneth |
| 6,218,661 | B1 | | 4/2001 | Schroeder et al. |
| 6,521,109 | B1 | | 2/2003 | Bartic et al. |
| 6,743,635 | B2 | | 6/2004 | Neel et al. |
| 7,074,519 | B2 | | 7/2006 | Kuhr et al. |
| 7,951,632 | B1 | | 5/2011 | Quick et al. |
| 8,202,697 | B2 | | 6/2012 | Holmes |
| 2002/0137998 | A1 | | 9/2002 | Smart et al. |
| 2002/0168290 | A1 | * | 11/2002 | Yuzhakov et al. .............. 422/56 |
| 2002/0177763 | A1 | | 11/2002 | Burns et al. |
| 2003/0088166 | A1 | | 5/2003 | Say et al. |
| 2003/0212344 | A1 | | 11/2003 | Yuzhakov et al. |
| 2003/0217918 | A1 | * | 11/2003 | Davies et al. ............ 204/403.02 |
| 2004/0002682 | A1 | | 1/2004 | Kovelman et al. |
| 2004/0039303 | A1 | | 2/2004 | Wurster et al. |
| 2004/0094432 | A1 | * | 5/2004 | Neel et al. ................... 205/777.5 |
| 2004/0136866 | A1 | | 7/2004 | Pontis et al. |
| 2004/0146863 | A1 | | 7/2004 | Pisharody et al. |
| 2004/0200721 | A1 | * | 10/2004 | Bhullar et al. ........... 204/403.01 |
| 2004/0254546 | A1 | | 12/2004 | Lefebvre |
| 2005/0183953 | A1 | * | 8/2005 | Su et al. ................... 204/403.01 |
| 2005/0238537 | A1 | | 10/2005 | Say et al. |
| 2005/0261606 | A1 | | 11/2005 | Sohrab |
| 2005/0279647 | A1 | | 12/2005 | Beaty |
| 2005/0287065 | A1 | | 12/2005 | Suddarth et al. |
| 2006/0113187 | A1 | | 6/2006 | Deng et al. |
| 2006/0211933 | A1 | | 9/2006 | Zimmermann et al. |
| 2007/0027384 | A1 | | 2/2007 | Brister et al. |
| 2007/0087492 | A1 | | 4/2007 | Yamanaka |
| 2007/0096164 | A1 | | 5/2007 | Peters et al. |
| 2008/0027302 | A1 | | 1/2008 | Buse et al. |
| 2008/0167578 | A1 | | 7/2008 | Bryer et al. |
| 2008/0197024 | A1 | * | 8/2008 | Simpson et al. ............... 205/778 |
| 2009/0018411 | A1 | | 1/2009 | Mace et al. |
| 2010/0270150 | A1 | | 10/2010 | Wang et al. |
| 2010/0274181 | A1 | | 10/2010 | Wang et al. |
| 2010/0298679 | A1 | | 11/2010 | Wu et al. |
| 2011/0180405 | A1 | | 7/2011 | Chinnayelka et al. |

FOREIGN PATENT DOCUMENTS

| | | |
|---|---|---|
| WO | WO 2010/033660 | 3/2010 |
| WO | WO 2010/033668 | 3/2010 |
| WO | WO 2010/033741 | 3/2010 |
| WO | WO 2010/033748 | 3/2010 |

OTHER PUBLICATIONS

International Preliminary Report on Patentability and Written Opinion of International Application No. PCT/US2009/032991 mailed Aug. 19, 2010.
International Search Report and Written Opinion of related International Application No. PCT/US2009/057253 mailed Nov. 2, 2009.
International Search Report and Written Opinion of related International Application No. PCT/US2009/057264 mailed Nov. 10, 2009.
International Preliminary Report on Patentability of related International Application No. PCT/US2009/057264 mailed Mar. 31, 2011.
International Preliminary Report on Patentability of related International Application No. PCT/US09/057382 mailed Mar. 31, 2011.
International Search Report and Written Opinion of International Application No. PCT/US09/057382 mailed Feb. 1, 2010.
International Preliminary Report on Patentability Search Report and Written Opinion of related International Application No. PCT/US2009/057253 mailed Mar. 31, 2011.
International Search Report and Written Opinion of International Application No. PCT/US2009/032991 mailed Aug. 6, 2009.
Communication pursuant to Rules 161(2) and 162 EPC of related European Application No. 09815226.7 May 12, 2011.
Communication pursuant to Rules 161(2) and 162 EPC of related European Application No. 09815166.5 May 13, 2011.
Communication pursuant to Rules 161(2) and 162 EPC of related European Application No. 09815223.4 May 12, 2011.
Communication pursuant to Rules 161(2) and 162 EPC of related European Application No. 09815172.3 May 25, 2011.
Singh et al., "SiC-C Fiber Electrode for Biological Sensing", Feb. 22, 2007, Materials Science and Engineering C, Elsevier Science S.A., vol. 27, No. 3, pp. 551-557.
International Search Report and Written Opinion of International Application No. PCT/US2009/057372 mailed Nov. 13, 2009.
International Preliminary Report on Patentability and Written Opinion of International Application No. PCT/US2009/057372 mailed Mar. 31, 2011.
Extended Search Report of related European Application No. 09815223.4 dated Oct. 2, 2012
Communication pursuant to Rules 70(2) and 70a(2) EPC of related European Application No. 09815223.4 dated Oct. 19, 2012.
Schackleford et al., CRC Materials Science and Engineering Handbook, 3rd ed., 2000, Table 154.
Extended Search Report of related European Application No. 09815166.5 dated Oct. 22, 2012.
Extended Search Report of related European Application No. 09815226.7 May 9, 2014.
Sengupta, D.K., et al. "Laser Conversion of Electrical Properties for Silicon Carbide Device Applications", Jour. Of Laser Applications, vol. 13, Jan. 1, 2011, pp. 26-31.
Wang et al., "Miniaturized Glucose Sensors Based on Electrochemical Codeposition of Rhodium and Glucose Oxidase onto Carbon-Fiber Electrodes," 1992, The American Chemical Society, vol. 64, pp. 456-459.

* cited by examiner

ANALYTE SENSORS, SYSTEMS, TESTING APPARATUS AND MANUFACTURING METHODS

RELATED APPLICATIONS

The present application claims priority to U.S. Provisional patent application No. 61/098,726 filed Sep. 19, 2008, and entitled "ANALYTE SENSORS, SYSTEMS AND MANUFACTURING METHODS" which is hereby incorporated herein by reference in its entirety for all purposes.

FIELD OF THE INVENTION

The present invention relates to electrochemical analyte sensors that may be used to detect an analyte concentration level in a bio-fluid sample, apparatus including the analyte sensors, and methods of manufacturing thereof.

BACKGROUND OF THE INVENTION

The monitoring of analyte concentration levels in a bio-fluid is an important part of health diagnostics. For example, an electrochemical analyte sensor may be employed for the monitoring of a patient's blood glucose level as part of diabetes treatment and care.

Such electrochemical analyte sensors may be employed discretely, for instance, by detecting an analyte concentration level in bio-fluid sample such as from a single sample of blood or other interstitial fluid obtained from the patient via a lancet (e.g., by a pin-prick or needle). In discrete monitoring, there is usually a separation between the bio-fluid sample collection process and the measurement of the analyte concentration level. Typically, after a bio-fluid sample has been obtained from the patient, such as by the use of a lancet, the sample is then transferred to a medium (e.g., a test strip sensor or a detector) for measurement of the bio-fluid sample's analyte concentration level.

Because of the relatively low sensitivity of some conventional electrochemical analyte sensors coupled with relatively inefficient transfer of the bio-fluid sample to the sensor, a relatively large sample volume may be required in order to yield an accurate measurement of the analyte concentration level. In such instances, if the provided sample has an insufficient sample volume, then either no reading or an inaccurate reading may result. Accordingly, an additional bio-fluid sample may need to be drawn and, consequently, lancet insertion may need to be repeated which may cause further pain and discomfort to the patient.

Additionally, conventional sensors may require the use of precious metals for the working and/or reference/counter electrodes which may add significantly to the cost of the analyte sensors.

It would, therefore, be beneficial to provide an analyte sensor adapted for bio-fluid analyte sampling that may consistently provide for analyte concentration level measurements from an obtained bio-fluid sample, which may require a relatively smaller sample volume, and/or which may also provide for lower cost manufacture.

SUMMARY OF THE INVENTION

In a first aspect, the present invention provides an analyte sensor including a hollow member having a hollow portion; a first conductor received in the hollow portion wherein the first conductor is comprised of a semiconductor material; and an active region in contact with at least the first conductor.

In another aspect, the present invention provides an analyte sensor for detecting an analyte concentration level in a bio-fluid sample. The analyte sensor includes a hollow member including a hollow portion; a first conductor including a semiconductor material received in the hollow portion; a cavity formed at least in part by walls of the hollow portion; and an active region positioned within the cavity and in contact with at least the first conductor.

In another aspect, the present invention provides an analyte sensor including a hollow member including a hollow portion and a lancet point formed on an end of the hollow member; a first conductor comprised of a semiconductor material included in the hollow portion; a cavity located proximate to an end of the first conductor; and an active region positioned within the cavity and in contact with at least the first conductor.

In another aspect, the present invention provides a testing apparatus including a port receiving an analyte sensor, wherein the analyte sensor further includes a hollow member including a hollow portion; a first conductor received in the hollow portion, the first conductor comprised of a semiconductor material; and an active region in contact with at least the first conductor.

In a system aspect, the present invention provides an analyte sensor system including a carriage having at least two guides; an analyte sensor received in each of the at least two guides wherein the analyte sensor includes a hollow member having a hollow portion and a lancet point, a first conductor received in the hollow portion, and an active region in contact with the first conductor.

In another system aspect, the present invention provides an analyte sensor system which includes a carriage having at least two guides; a lancet received in at least one of the guides; and an analyte sensor received in another of the guides.

In a method aspect, the present invention provides a method of manufacturing an analyte sensor providing a hollow member including a hollow portion; and receiving and securing a first conductor in the hollow portion wherein the first conductor is comprised of a semiconductor material, and an active region is applied to the first conductor.

Other features and aspects of the present invention will become more fully apparent from the following detailed description, the appended claims and the accompanying drawings.

DETAILED DESCRIPTION

Figure 1:
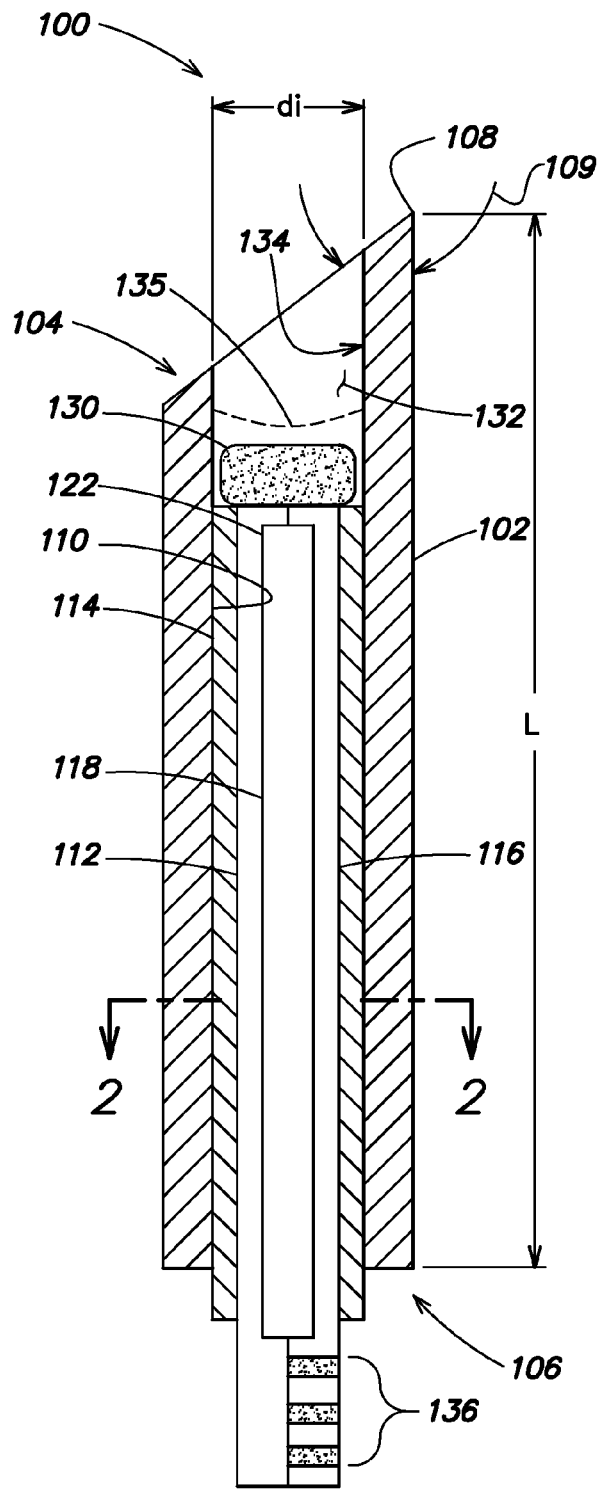
FIG. 1 is a cross-sectioned side view of an exemplary embodiment of an analyte sensor according to the present invention.

According to a first aspect of the present invention, an analyte sensor is provided that includes a hollow member having a hollow portion. A first conductor may be received in the hollow portion and may function as a working, reference and/or counter electrode, for example. In some embodiments, the hollow member may be formed from a stainless steel or similar rigid material and may have one sharpened end which may serve as a lancet. The analyte sensor may include a cavity formed near an end of the conductor within the hollow member to assist in bio-fluid collection.

The first conductor may include a semiconductor material, such as silicon carbide for example. In some embodiments, the first conductor may be a silicon carbide fiber, which may include a semiconductor material. For example, the fiber may have a core including a conductive material and a cladding including a semiconductor material. An active region may be provided in contact with at least the first conductor, and may be provided in the cavity. The active region may include one or more catalytic agents and/or reagents adapted to react and convert an analyte in a bio-fluid sample received in the cavity into reaction products from which an electrical current may be generated. This current may then be carried in a circuit including the first conductor to a testing apparatus (e.g., meter) and a display of an analyte concentration may be accomplished. The analyte sensor of the invention may provide for a very small required bio-fluid sample size, may reduce discomfort in obtaining the bio-fluid sample, and may be manufactured at relatively low cost.

In some embodiments, a second conductor may also be received in the hollow portion adjacent to the first conductor, and may operate as a reference or counter electrode, for example. The second conductor may also include a semiconductor material, and in some embodiments may have a conductive core and a cladding including a semiconductor material. As with the first conductor, the second conductor may also be provided in contact with, and electrically coupled to, the active region. In some embodiments, a conductive core of the first conductor and even the second conductor may comprise carbon (e.g., graphite) and the cladding may comprise silicon carbide. In a supplemental aspect, the hollow portion may also receive a third conductor which may function as a fill detector. In particular, the fill detector may be provided by including a fill detection electrode to detect when there is sufficient required volume of a bio-fluid sample present to accomplish an accurate measurement.

Thus, it should be apparent that in some embodiments, the first, second, and/or third conductors may be received and secured in the hollow portion of a hollow member. Because of the relatively small diameter of the conductors, the overall sensor diameter may also be made relatively small. In some embodiments, the hollow member may be a hollow lancet, while, in other embodiments, the hollow member may be a sleeve without a lancet point.

These and other embodiments of analyte sensors, apparatus and systems including the analyte sensors, and methods for manufacturing the analyte sensors are described below with reference to FIGS. 1-11. The figures are not drawn to scale.

Figure 2:
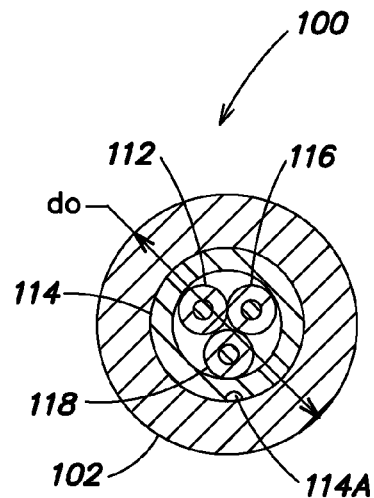
FIG. 2 is an end view of the analyte sensor of FIG. 1 taken along section line 2-2.
Figure 3:
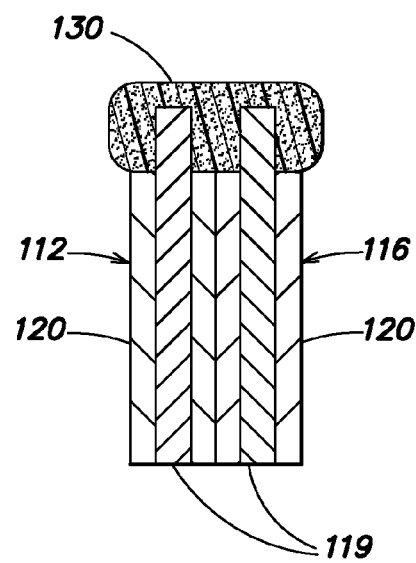
FIG. 3 is a partial sectioned end view illustrating the active region and connection to the conductors.

FIGS. 1-3 show various views of a first exemplary embodiment of an analyte sensor 100 provided according to the present invention. The analyte sensor 100 may include a hollow member 102 in the form of a hollow lancet. The hollow member 102 may be slender and needle-like and may be formed from any rigid material such as a metal (e.g., stainless steel) or other suitable material. The hollow member 102 may include a first end 104 and a second end 106. A lancet point 108 may be formed on the first end 104 and may be cleaved or otherwise formed at an angle 109 of between about 25 and 50 degrees, or even about 35 degrees, for example. Simply, the second end 106 may be terminated at a right angle to the axial length, for example. The hollow member 102 may further include a hollow portion 110, which may extend along a length of the hollow member 102. In some embodiments, the hollow portion 110 may comprise a hole of generally constant diameter, for example. Other suitable shapes may be used. The hollow member 102 may have a length (L) of between about 10 mm and about 75 mm, an outer diameter (do) of between about 200 microns and about 75 microns, and an inner diameter (di) of between 175 microns and about 50 microns. Other lengths and diameters may be used.

A first conductor 112 may be received in the hollow portion 110 and may extend along a portion of the length (L) thereof. The first conductor 112 may also be received in a hollow portion of a sleeve 114, which may locate and secure the conductor 112 in an axial and radial direction and may aid in the packaging and assembly of the analyte sensor 100. The sleeve 114 may be secured in the hollow portion 110 by any suitable means, such as by a press fit, mechanical fastening, adhering by the use of an adhesive, or by thermal bonding for example. The sleeve may be an insulating material. Adhesive or potting compound may be used to secure the first conductor 112 into the sleeve 114. Optionally, the conductor 112 may be received in the hollow portion 110 without the use of a sleeve 114, such as by the use of an adhesive or other bonding agent, for example. Of course, the first conductor 112 should be electrically insulated from the hollow portion 110, if that portion is made from an electrically-conductive material.

Additional conductors, such as a second conductor 116 and/or a third conductor 118, may also be received in the hollow portion 110 and may be secured in the same or similar manner as specified for the first conductor 112. Again, the conductors should be electrically insulated from each other. This may be accomplished through proper placement in the hollow member 110 via use of an insulating potting compound, such as when a sleeve 114 is not used. Optionally, or in addition, the conductors 112, 116, 118 may include an insulating layer (not shown) about their periphery and along their length to insulate the conductors electrically from one another. The insulating layer may be any suitable insulating material, such as a thin insulating layer. The layer may be a polymer material of suitable thickness to insulate the conductors from one another, such as polypropylene, polycarbonate, polytetraflourethylene, or the like. As best shown in FIG. 3, which is partial cross-sectioned view of the ends of the first and second conductors 112, 116, each of the conductors 112, 116 may include a semiconductor material. For example, the conductors 112, 116 may include a core 119, which may be comprised of a conductive material, and a cladding 120, which may be comprised of the semiconductor material.

In some embodiments, the first conductor 112 may be a fiber. In such fiber embodiments, the conducting core 119 may be at least partially surrounded by the cladding 120. The other conductors 116, 118 may be fibers also. In the exemplary embodiment shown in FIGS. 1-3, the cladding 120 may include an annular shape, which may fully surround the core 119 along at least a portion of the length of the core 119. The core 119 may comprise the shape of a cylindrical rod, for example. Both the core 119, which includes conductive material, and the cladding 120, which may comprise a semiconductor material, in operation may convey electrical current, albeit the semiconductor material typically includes a much higher resistivity as compared to the core 119 and, therefore, may, in some embodiments, carry less current than the core 119.

In more detail, the core 119 may comprise carbon (e.g., graphite) and the cladding 120 may comprise silicon carbide (SiC). SiC fibers having a suitable SiC cladding and carbon core are manufactured by Specialty Materials Inc. of Lowell, Mass., for example. However, the conductive material of the core 119 may also comprise other electrically conductive materials, including noble metals (e.g., gold, silver, platinum, palladium, or the like), or other metals (e.g., copper and aluminum) and the cladding 120 may comprise other semiconductor materials including Group IV elements such as silicon and germanium, Group IV compounds such as silicon germanide (SiGe), and Group III-V compounds such as gallium arsenide (GaAs) and indium phosphide (InP), among others.

In some embodiments, the first conductor 112 may have a total diameter (including the core 119 and cladding 120 of about 150 microns or less, about 100 microns or less, about 75 microns or less, or even about 50 microns or less (although larger or smaller sizes may also be used). The core 119 may have a diameter between about 10 microns to about 100 microns, or even between about 20 microns to about 40 microns. In some embodiments, core 119 may have a diameter of about 30 microns, although other dimensions may also be used.

In the depicted embodiment of FIG. 3, the first conductor 112 may include an end portion where the core 119 is exposed (the 'stripped end'). This may enlarge and enhance an effective contact area, and thus the conducting area, of the conductive core 119 such as when the core 119 functions as a working electrode. Any suitable technique may be used to remove the cladding material thereby forming the stripped end, such as machining, etching, or the like. Etching may include electrochemical wet etching with an acid (e.g., HF). Other mechanisms for enhancing the effective contact area of the core 119 may be used. The second conductor 116 may include a similar construction.

Again, the analyte sensor 100 may further include a second conductor 116 received in the hollow portion 110. The materials and sizes for the second conductor 116 may be the same as described above for the first conductor 112. However, the second conductor 116 may be, as shown in FIG. 1, another fiber comprised of a semiconductor material and which may be oriented in a generally parallel relationship alongside the first conductor 112 in the hollow portion 110. The second conductor 116 may function as a reference electrode providing a return path for an electrical current. In one or more embodiments, the second conductor 116 may function as a counter electrode. It should be recognized that the second conductor 116 may take on other forms (e.g., a coil, foil, strip, or film) and may be made from other suitable electrically conductive materials. For example, the second conductor 116 may be manufactured from more conventional materials, such as carbon, graphite, silver, gold, palladium, or platinum.

The third conductor 118 may also be received in the hollow portion 110 and may provide for a fill detection function, as will be described below in more detail. The third conductor 118 may be made of the same materials and general size as in the previous embodiments, but may be slightly shorter, for example.

Referring now to FIGS. 1 and 3, applied onto the first conductor 112, and in contact with and electrically coupled to the first conductor 112 at the end thereof, is an active region 130 to be described below more thoroughly. Briefly, however, the active region 130 is adapted to be exposed to the bio-fluid sample. The active region 130 may include one or more catalytic agents or reagents and may be adapted to promote an electrochemical reaction between an analyte in the bio-fluid sample and the catalytic agents or reagents. This may produce reaction products and mobile electrons, which then may be conducted, for example, by the core 119 and/or cladding 120 of the first conductor 112. A mediator, to be described below, may be provided in the active region 130 to aid in carrying the electrons to the surface of the first conductor 112, and may further reduce a potential required for a redox reaction.

According to some embodiments of the invention, a cavity 132 may be formed and provided proximate to a working end of the first conductor 112 in the proximity of the active region 130. The cavity 132 may receive a bio-fluid sample from the insertion of the lancet point 108 into the body part (not shown). In particular, the cavity 132 may be at least partially formed and defined, for example, by inner surfaces (walls) 134 of the hollow portion 110, and surfaces of the sleeve 114 (if present), the active region 130, and the end of the third conductor (if present). The cavity 132 may have any shape, but preferably has a shape, which promotes capillary action to cause a droplet of bio-fluid to, drawn in and come to rest adjacent to the active region 130. To promote capillary action, the cavity 132 may include a depth of between about 1 to about 3 times the inner diameter (di) and may include one or more vent holes 114A formed in a side of the sleeve 114. The term "cavity" as defined herein is an indented or concave area having walls and which is adapted to contain and/or at least partially confine the bio-fluid sample.

In some embodiments, a sufficient bio-fluid sample for purposes of detecting an analyte concentration level may have a volume of less than about 0.5 microliters, less than about 0.4 microliters, less than about 0.3 microliters, or even less than about 0.2 microliters, for example. Other sample volumes may also be employed. Thus, excellent analyte detection may be accomplished with a relatively small sample size of the bio-fluid. Accordingly, the propensity to have to prick a finger, etc., a second time to obtain sufficient fluid volume for testing may be reduced or eliminated. Further, with an embodiment such as depicted in FIGS. 1-3, which includes an integrated lancet and analyte sensor, the need to transfer the fluid is eliminated.

Referring to FIGS. 2 and 3, the active region 130 may be positioned within the cavity 132, and is preferably located at a bottom of the cavity 132, thereby allowing exposure of the active region 130 to the sample of bio-fluid that enters the cavity 132 through capillary action. As best shown in FIG. 3, the active region 130 may be applied over, and in contact with, the cores 119 of the first and second conductors 112, 116. For example, the active region 130 may be applied to the stripped cores 119, as shown. Optionally, an enhanced conductive region may be locally produced by subjecting the fiber's SiC cladding to intense localized heat and thereby causing a significant change in the resistivity and/or activity of the SiC cladding material. Thereafter, the active region 130 may be applied to this enhanced region.

Figure 4:
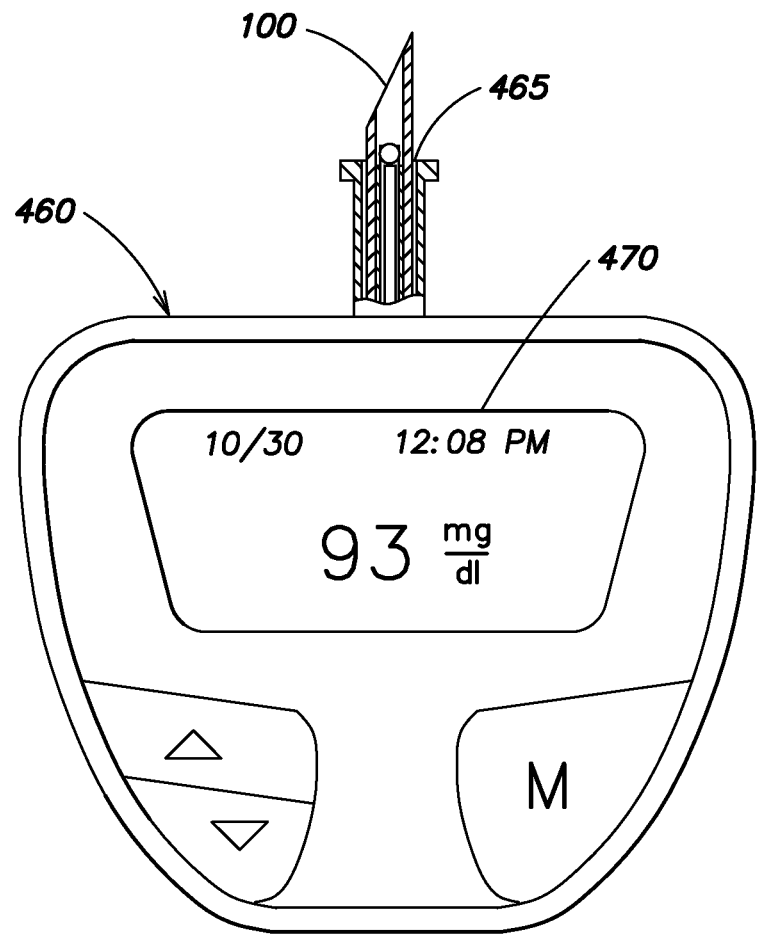
FIG. 4 is a testing apparatus including an analyte sensor of the invention.

Upon insertion of the bio-fluid sample into the cavity 132, an electrochemical reaction may take place between the analyte in the bio-fluid sample and the catalytic agents or reagents of the active region 130. This may produce reaction products and generate a flow of electrons in the first and second conductors 112, 116. The cores 119 and/or claddings 120 may then conduct and channel the electron flow and provide an electrical current, which may be proportional to the concentration of the analyte in the bio-fluid sample. This current may then be conditioned and displayed in any suitable readout form, such as in a digital readout 470 of a testing apparatus 460 (e.g., such as shown in FIG. 4).

Again referring to FIGS. 1-3, one group of catalytic agents useful for providing the active region 130 is the class of oxidase enzymes which includes, for example, glucose oxidase (which converts glucose), lactate oxidase (which converts lactate), and D-aspartate oxidase (which converts D-aspartate and D-glutamate) and alcohol oxidase or alcohol dehydrogenase (which converts alcohol). In embodiments in which glucose is the analyte of interest, glucose dehydrogenase (GDH) may optionally be used. Pyrolloquinoline quinine (PQQ) or flavin adenine dinucleotide (FAD) dependent may also be used. A more detailed list of oxidase enzymes which may be employed in the present invention is provided in U.S. Pat. No. 4,721,677, entitled "Implantable Gas-containing Biosensor and Method for Measuring an Analyte such as Glucose" to Clark Jr. which is hereby incorporated by reference herein in its entirety. Catalytic enzymes other than oxidase enzymes may also be used.

The active region 130 may include one or more layers (not explicitly shown) in which the catalytic agents (e.g., enzymes) and/or other reagents may be immobilized or deposited. The one or more layers may comprise various polymers, for example, including silicone-based or organic polymers such as polyvinylpyrrolidone, polyvinyl alcohol, polyethylene oxide, cellulosic polymers such as hydroxyethylcellulose or carboxymethyl cellulose, polyethylenes, polyurethanes, polypropylenes, polyterafluoroethylenes, block co-polymers, sol-gels, etc. A number of different techniques may be used to immobilize the enzymes in the one or more layers in the active region 130 including, but not limited to, coupling the enzymes to the lattice of a polymer matrix such as a sol gel, cross-linking the agents to a suitable matrix such as glutaraldehyde, electropolymerization, and formation of an array between the enzymes via covalent binding, or the like.

In some embodiments, an electrochemically active layer (not explicitly shown) may be deposited and positioned adjacent to an exposed end (e.g., the stripped portion) of the core 119. The electrochemically active layer may include, for example, noble metals such as platinum, palladium, gold, rhodium, or other suitable materials. In a glucose detection embodiment, the active layer may undergo a redox reaction with hydrogen peroxide when polarized appropriately. The redox reaction causes an electrical current to be generated by electron transfer that is proportional to the concentration of the analyte that has been converted into hydrogen peroxide. This current may be conducted and conveyed from the electrochemically active layer through the core 119 and/or cladding to a testing apparatus such as the one described with reference to FIG. 4 herein.

Additionally, in some embodiments a mediator may be included within the active region 130 to promote the conversion of the analyte to detectable reaction products. Mediators comprise substances that act as intermediaries between the catalytic agent and the working electrode (e.g., the surface of the exposed core, a surface area enhancement of the core, the cladding, or an electrochemically active layer applied to the core, etc.). For example, a mediator may promote electron transfer between the reaction center where catalytic breakdown of an analyte takes place and the working electrode, and may enhance electrochemical activity at the working electrode. Suitable mediators may include one or more of the following: metal complexes including ferrocene and its derivatives, ferrocyanide, phenothiazine derivatives, osmium complexes, quinines, phthalocyanines, organic dyes as well as other substances. In some embodiments, the mediators may be cross-linked along with catalytic agents directly to the working electrode.

To form an electrochemical cell, the second conductor 116 may also be coupled to the active region 130 in the cavity 132. In particular, the active region 130 may be applied so as to be in contact with and configured to extend between the cores 119 (or cladding 120) of the first and second conductors 112, 116 at the ends thereof. The active region 130 may extend along the generally opposed surfaces of the cores 119 (or claddings 120), such that a drop of bio-fluid (depicted by dotted line 135 in FIG. 1) is received in a three dimensional feature formed by the active region 130 as applied over the surfaces of first and second conductors 112, 116.

Additionally in the depicted embodiment of FIG. 1 and in the other embodiments described herein, one or more of the members 112, 116, 118 of the analyte sensor 100 may be provided with a coded region 136. The coded region 136 may allow information about the sensor to be coded onto one or more of the conductors 112, 116, and 118. The coded information may relate to information about and/or properties or features of the analyte sensor 100. For example, the date of manufacture, lot number, part number or version number, calibration data or constants, and/or expiration date of the sensor may be encoded.

The coded region 136 may be formed of and include one or more conductive portions (e.g., rings or conductive dots). The conductive portions may be formed on an outer portion of the conductor, such as on the cladding 120, for example. In the depicted embodiment, three conductive portions are shown. However, a greater or lesser number of conductive portions may be used. For example, in one embodiment, a single track of variable width may be used, wherein a two-point measurement of resistance may be taken to measure and determine a level of resistance. The resistance value may vary with the width of the track, or its processing, for example. That resistance value may then be correlated to a code in a lookup table, for example.

In another embodiment where the conductor is a SiC fiber, a coded region 136 such as a conductive track or ring may be formed, for example, by subjecting the SiC cladding 120 of the conductor 112, 116, and/or 118 to intense localized heat. For example, the cladding 120 may be exposed to a laser beam emitted from a laser. Other high intensity heat sources may be used, such as thermal plasmas for example. The intense localized heating of the cladding 120 comprised of SiC may cause a relatively large localized change in resistivity of the SiC cladding. As such, the localized heating may provide a track or ring encircling the core 119 having a changed resistivity which may preferably penetrate into the depth of the core 119. The track may exhibit significantly different resistivity (e.g., several orders of magnitude or more) than the surrounding SiC material that has not been subjected to the heat treatment.

In the depicted embodiment, a plurality of spaced, tracks or rings may be provided on the conductor 116. The tracks positioned on the conductor 116 may be used to provide bits of coded information (e.g., 1's and 0's) which thereafter may be read by a suitable reader provided in the testing apparatus (not shown). For example, a track existing at a defined location spaced from the terminal end of the conductor 116 may be used to signify a "1," while the absence of a track at a defined location may indicate a "0." Accordingly, with only 4 predetermined track locations, $2^4$ bits or 16 codes may be provided which then may be read by a testing apparatus (not shown), for example. A multi-contact electrical contact (not shown) may be used to determine the presence or absence of a track or ring at each spaced location. In some embodiments, in the alternative or in addition, it may be desirable to code information on another one or more of the other conductors (e.g., 112 and/or 118).

In accordance with another aspect of the invention, the third conductor 118 may be used to provide a fill detector which may provide a fill volume detection function in the analyte sensor 100. An end 122 of the conductor 118 may be provided proximate to the active region 130 to ensure that a sufficient bio-fluid sample is present when performing a detection of an analyte concentration. In the depicted embodiment, the fill detection is provided by positioning the end 122 of the conductor 118 slightly offset (in an axial direction) from a location of the active region 130. The end of the conductor 118 is located and included in the cavity 132.

In operation, if a sufficient bio-fluid sample is present, a portion of the bio-fluid sample may come to rest on the end 122 of the conductor 118 and may complete an electrical circuit between the second conductor 116 (reference conductor) and the third conductor 118, for example. In other words, the presence of the bio-fluid may provide a conductive path through the bio-fluid sample completing a circuit. Optionally, the body of the hollow member 102 (if conductive) may be used as an electrical path to complete a circuit for fill detection. Accordingly, when a sufficient bio-fluid sample is present and detected at the location of the fill detector, then a measurement of the analyte concentration may be made.

As further shown in FIG. 4, an embodiment of the analyte sensor 100 described with reference to FIGS. 1-3, or any of the additional embodiments described herein, may be inserted and received into a port 465 of a testing apparatus 460. The analyte sensor 100 has been shown as being enlarged and in an extended position for clarity. Electrical contacts (See FIG. 10, for example) in the testing apparatus 460 may come into electrical contact with a conductive ends of the first, second and third conductors 112, 116, 118 thereby making an electrical connection to the circuitry of the apparatus 460. Upon applying a suitable voltage bias, conventional processing programs and circuitry may then equate the current supplied by the analyte sensor 100 to an analyte concentration level, which then may be displayed on a digital display 470. The analyte sensor 100 may be included in a carriage and may be loaded into the port 465 from the interior of the apparatus 460. Any suitable method may be employed to extend and retract the sensor 100, such as a user-cocked, spring loaded and trigger released mechanism, or an electromagnetically actuated mechanism.

Figure 5:
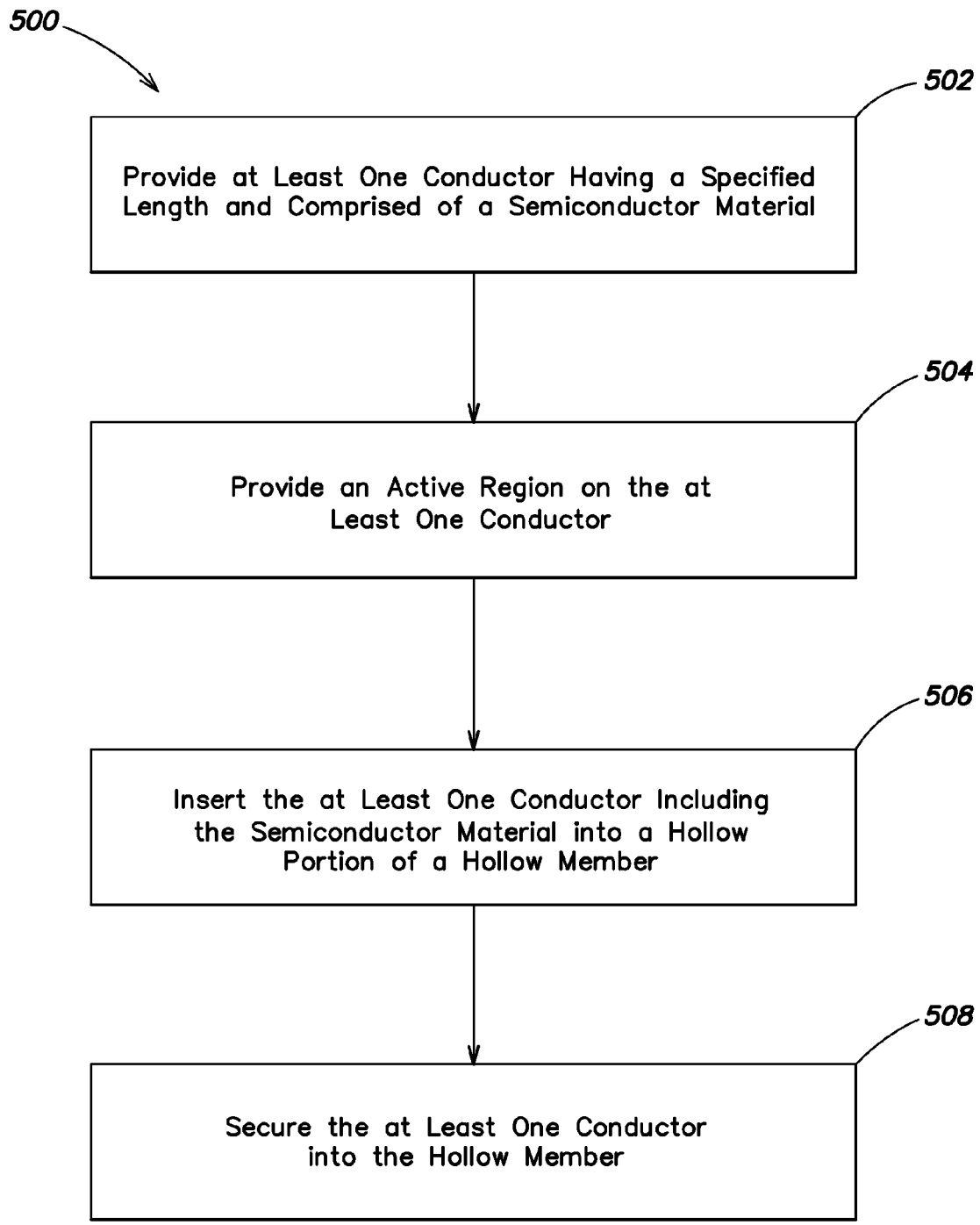
FIG. 5 is a flowchart illustrating methods of manufacturing an analyte sensor according to the present invention.

Methods for manufacturing analyte sensors of the invention will now be described with reference to FIG. 5. According to the method 500, in step 502, at least one conductor, and in some embodiments a number of the conductors (e.g., 112, 116, 118), may be provided and may be cut to a specified length, for example. The at least one conductor (e.g., 112) may be comprised of a semiconductor material. For example, the conductor may include a conductive core and a semiconductor cladding. According to some embodiments where multiple conductors are employed, the first and second conductors 112, 116 may have been, in a previous step, secured together such as by an adhesive or potting compound. The conductors 112, 116 have been electrically insulated from one another along their length as described above herein.

In step 504, an active region is applied to the end of the at least one conductor. When two conductors are employed, an active region may be applied to an end of the first and second conductors simultaneously so to form a bridge of the active material connecting between the ends of the conductors. The active region may be applied to the conductors by a layer-to-layer deposition technique, dipping, spraying, dot drop, screen print, or the like. The active region may be formed such that it may provide a continuous connection between the conductors. The conductors may then be inserted into and secured in a hollow portion of a sleeve of polymer material, such as a polycarbonate material, by friction or by an adhesive or potting compound. The conductors may extend slightly out of the end of the sleeve such that the active region will be housed and exposed in the cavity and so that the ends of conductor are readily accessible. The subassembly including at least one conductor and the sleeve may then be inserted and received into the hollow portion of the hollow member in step 506. The subassembly may be secured in spaced registry with the first end of the hollow member such that the cavity is formed with the active region included in the cavity. The subassembly, and thus the at least one conductor may be secured by adhesive or press fit in step 508.

Where fill detection is present, a conductor may be oriented axially relative to the active region and adhered in place prior to insertion into the sleeve. Optionally, one or more of the conductors may include one or more coded regions, which may be used to code various features, properties and/or information concerning the analyte sensor. The conductors may be preprocessed to include several regions of differing conductivity or resistivity for providing coded information.

Figure 6:
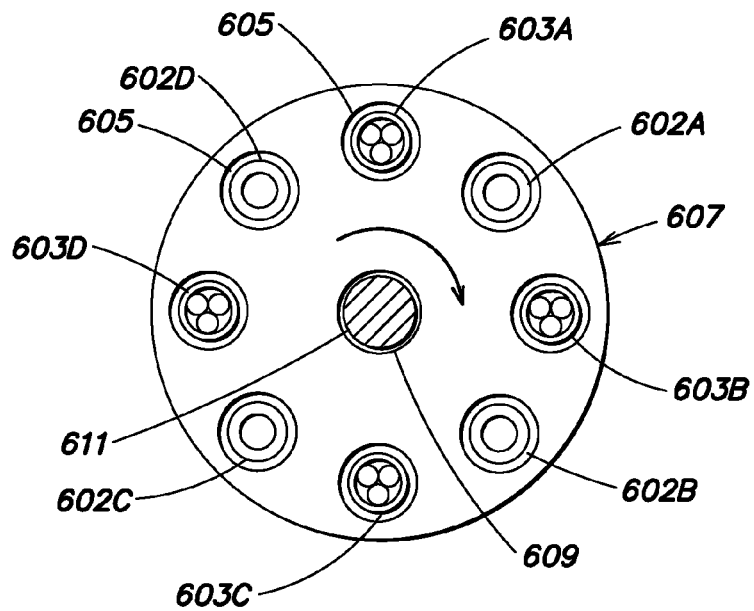
FIG. 6 is a top view of an exemplary embodiment of a rotatable carriage according to the present invention.
Figure 7:
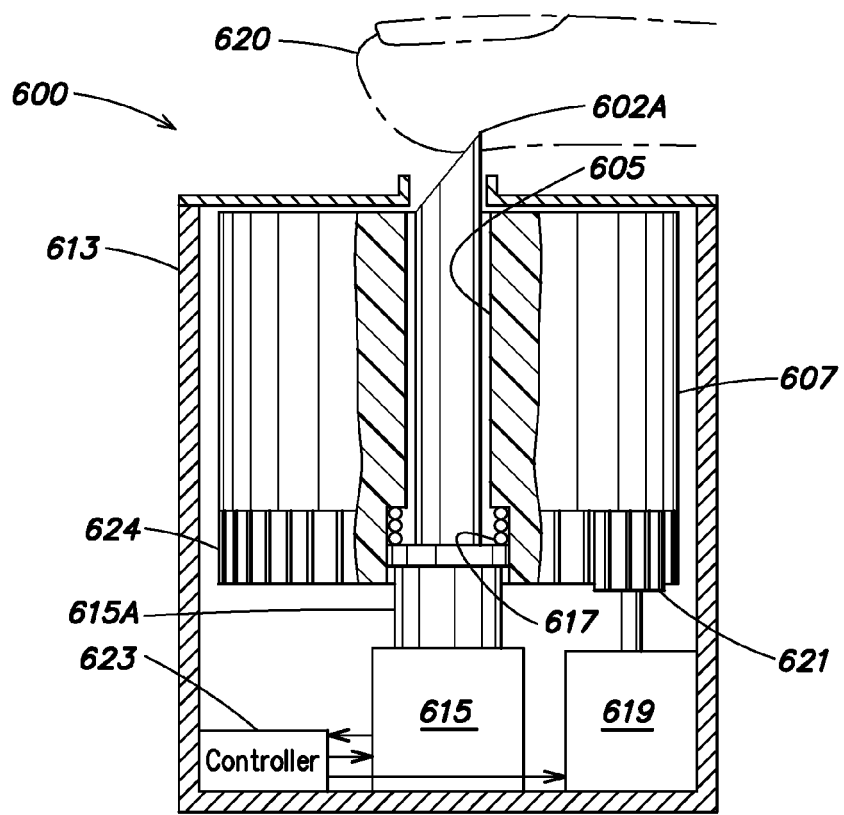
FIG. 7 is a partially cross-sectioned side view of an exemplary embodiment of a rotatable carriage according to the present invention.

FIGS. 6-9 depict an embodiment of an analyte sensor assembly 600. In this embodiment, the lancets 602A-602D and the analyte sensors 603A-603D are received in guides 605 formed in a rotatable carriage 607. The carriage 607 is shown in FIG. 6 without showing other structure of the assembly for clarity. The carriage 607 may be cylindrically shaped and may include guides 605. The guides 605 may be axially oriented (such as the generally parallel circular holes shown) and may be formed in a circular pattern. These guides 605 may form channels for the lancets 602A-602D and analyte sensors 603A-603D to extend and retract within. A central aperture 609 in the carriage 607 may cooperate with a post 611 of a housing 613 to allow for unidirectional rotation of the carriage 607, as shown by the arrow in FIG. 6.

In operation, an actuator member 615A, which is a moving portion of an actuator 615, is caused to abruptly contact an end of the lancet 602A causing the lancet 602A to slide in the guide 605 of the carriage 607 and extend into contact with a user's body part 620 (e.g., finger or thumb—shown dotted). Again, the lancet 602A is shown enlarged for clarity. A retraction mechanism, such as a spring 617, may be operable with the lancet 602A to cause the lancet 602A to retract from the extended position shown in FIG. 7. The actuator 615 may be any suitable actuator, such as a linear actuator, solenoid, or other electromagnetic mechanism, which may provide sufficient force to cause the lancet 602A to lance the user's body part 620. Optionally, the mechanism may be a user cocked, spring loaded and trigger releasable mechanism.

Figure 8:
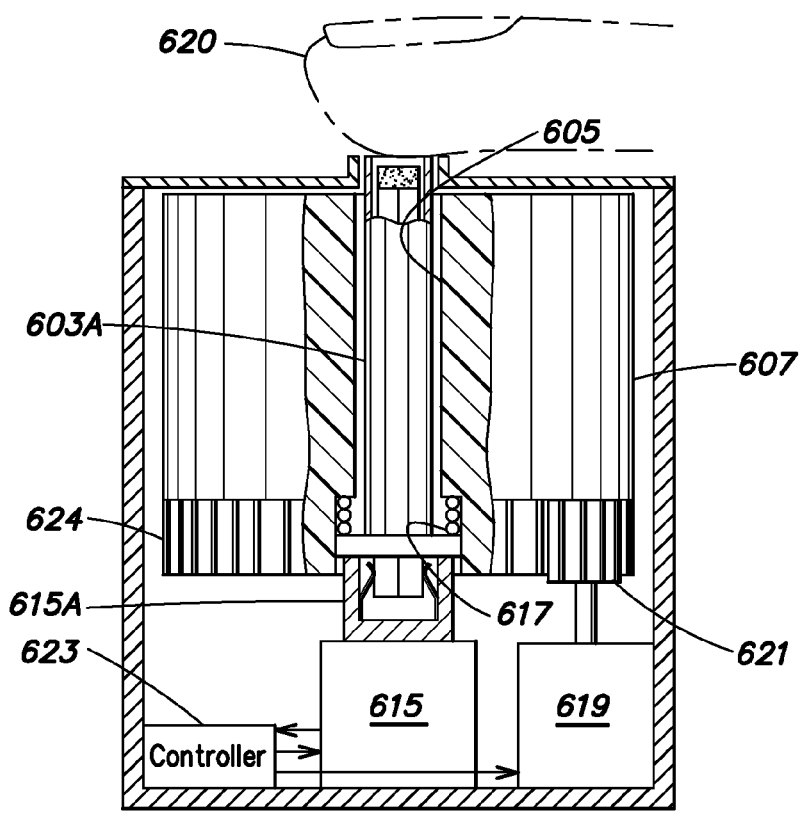
FIG. 8 is a partially cross-sectioned side view of an exemplary embodiment of a system including the rotatable carriage of FIG. 7 depicting the carriage rotated to actuate an analyte sensor according to the present invention.

Upon retraction of the lancet 602A, the carriage 607 may be caused to rotate. Rotation may be caused by any suitable mechanism, such as a manual dial mechanism or by a motor 619 and gear assembly shown. For example, the motor 619 may rotate a gear 621, which meshes with gear teeth 624 formed on a molded plastic carriage 607. The rotation of the carriage 607 may cause the sensor 603A, as best shown in FIG. 8, to rotate into alignment with the actuator member 615. Once rotated into alignment, the actuator member 615A may cause the sensor 603A to extend into contact with the lancing site on the user's body part 620 and collect a bio-fluid sample through capillary action.

Figure 9:
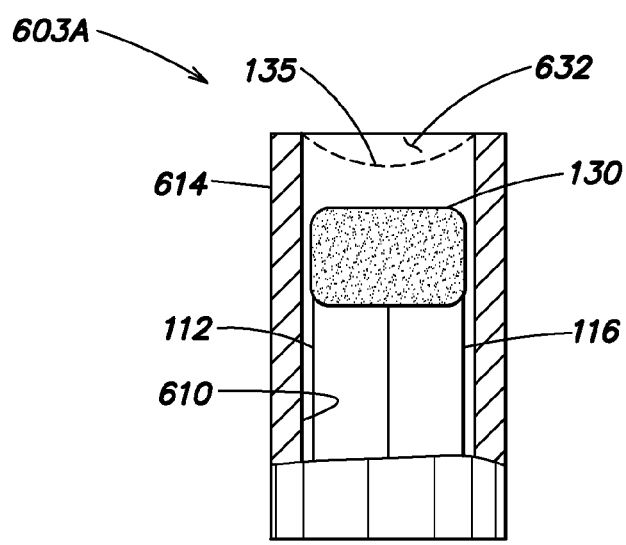
FIG. 9 is a partial cross-sectioned view of an exemplary embodiment of the analyte sensor of FIG. 7 according to the present invention.

FIG. 9 provides a partial enlarged breakout view of an end of the sensor 603A of FIG. 8 that is in contact with the body part 620 after the lancing operation has taken place. In this sensor embodiment, the hollow member 614 comprises a sleeve and the conductors 112, 116 are received in the hollow portion 610 of the hollow member 614 in a like manner as described before for sleeve 114. The conductors 112, 116 are insulated from one another as described above herein. However, in this embodiment, the sleeve 614 is not received in a hollow lancet and the sleeve itself comprises the hollow member. To form a cavity 632, the active region 130 interconnected between the first and second conductors 112, 116 and is spaced from the end of the sleeve 614. In this manner, the sample of bio-fluid may be drawn into the cavity 632 by capillary action so that a measurement of the analyte concentration may be accomplished. The other manufacturing steps for the analyte sensor 630A are as described with reference to FIG. 5. As is shown in FIG. 8, electrical contacts in the actuator member 615A may contact the ends of the conductors 112, 116 such that a connected controller 623 may calculate and display on a LCD display (not shown) an analyte concentration reading. The ends of the conductors 112, 116 may be made free of any insulating material in the area where electrical contact with the electrical contacts is made.

Figure 10:
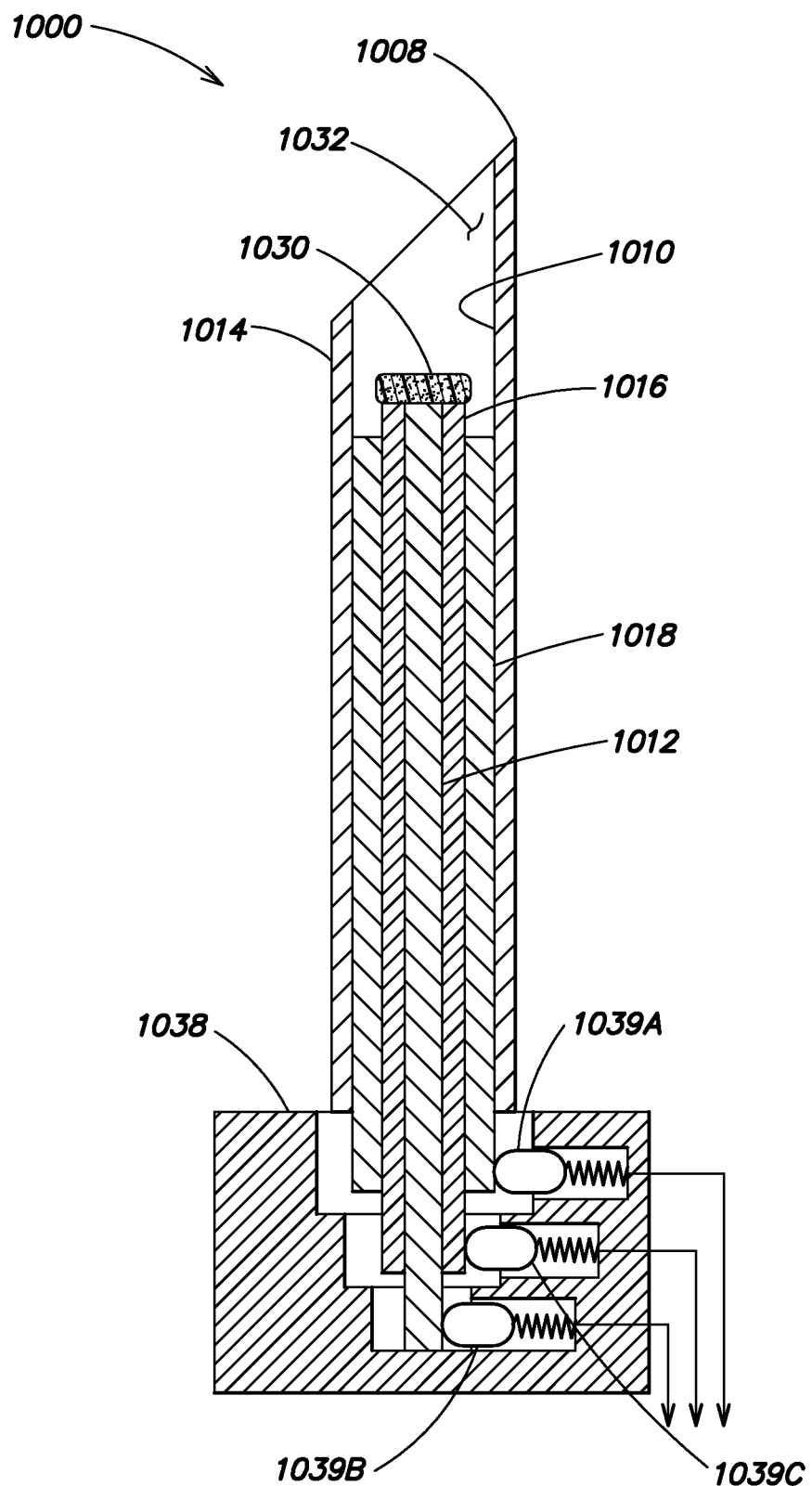
FIG. 10 is a cross-sectioned view of another exemplary embodiment of an analyte sensor according to the present invention.

FIG. 10 illustrates another embodiment of an analyte sensor 1000 according to the present invention. In this analyte sensor embodiment, a hollow member 1014 is provided which is comprised of a cylindrical sleeve having a lancet point 1008 on one end. Conductors 1012, 1016, and 1018 are received and secured in a hollow portion 1010 of the hollow member 1014. The conductors 1012, 1016, and 1018 may be secured in the hollow member 1014 by press fit or by any suitable bonding mechanism, such as an adhesive. The conductors 1012, 1016, 1018 in this embodiment may have a common centerline, i.e., they may be concentric. Each conductor 1012, 1016, and 1018 is insulated from the adjacent one by an insulating layer (not explicitly shown) and each conductor may be of a different length to facilitate ease of electrical connection thereto.

To form a cavity 1032, the active region 1030 interconnected between the first and second conductors 1012, 1016 may be provided in a spaced orientation from the end of the hollow member 1014 as is the third conductor 1018 which may provide a fill detector. In this manner, the sample of bio-fluid may be drawn into the cavity 1032 by capillary action, and when a sufficient sample is detected, a measurement of the analyte concentration may be accomplished. The other manufacturing steps for the analyte sensor 1000 are as described with reference to FIG. 5.

Figure 11:
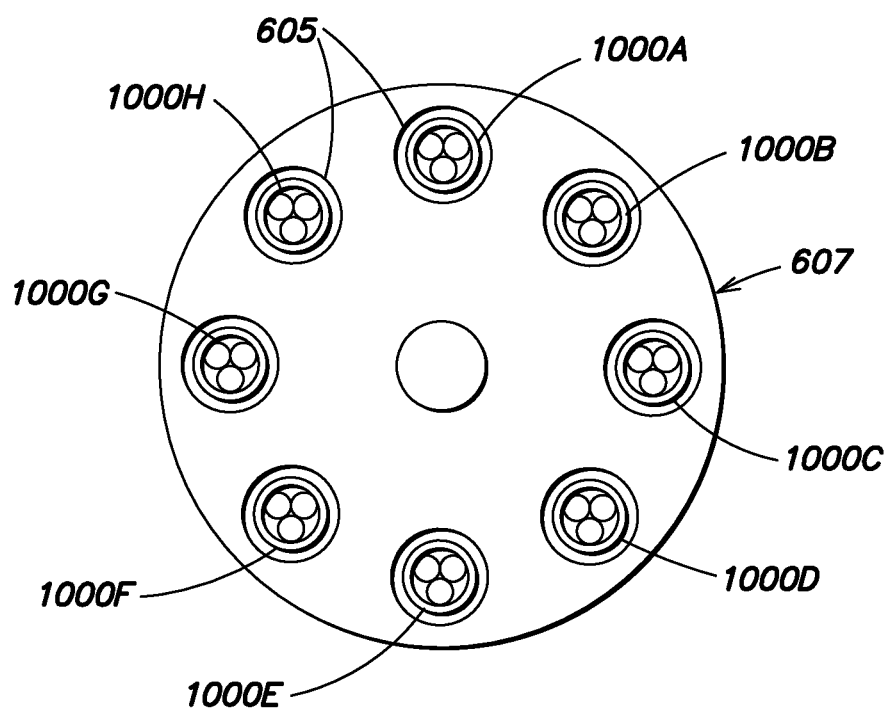
FIG. 11 is a top view of another exemplary embodiment of a rotatable carriage according to the present invention.

Also shown in FIG. 10, is one embodiment of an electrical connection that may be made with the analyte sensor 1000. In the depicted embodiment, an electrical contact assembly 1038 including one or more laterally moveable electrical contacts 1039A, 1039B, 1039C may contact a conductive portion of each of the conductors 1012, 1016, 1018, for example. Insulating material may not be provided or may be removed in the area where electrical contact with the contacts 1039a, 1039b, 1039c is made. The assembly 1038 may be included in a meter (not shown) and facilitate providing electrical signals to the processing electronics and/or circuitry of the meter. As should be recognized, the assembly 1038 may be used as an alternative configuration of the moving actuator member (e.g. 615A in FIG. 8) or may be contacted by a striking member of a user-cocked and trigger releasable mechanism) not shown). It should be understood that each of the analyte sensors shown in FIG. 1 and FIG. 10 may be employed in the carriage apparatus shown in FIG. 6. In other words, as best illustrated in FIG. 11, the carriage 607 may be loaded with integrated lancet and sensor embodiments of FIG. 1 or FIG. 10 only, designated as 1000A-1000H. In this case, a single actuation of an actuator member may extend an analyte sensor 1000A-1000H in a guide 605 and be used to simultaneously lance and sense analyte concentration.

The foregoing description discloses only exemplary embodiments of analyte sensors, apparatus including the same, and methods of manufacturing the analyte sensors of the invention. Modifications of the above disclosed analyte sensors, apparatus incorporating them, and methods for manufacturing them which fall within the scope of the invention will be readily apparent to those of ordinary skill in the art.

Accordingly, while the present invention has been disclosed in connection with exemplary embodiments thereof, it should be understood that other embodiments may fall within the spirit and scope of the invention, as defined by the following claims.

The invention claimed is:

1. An analyte sensor, comprising:
    a hollow cylindrical member including an inner wall defining a hollow portion;
    a hollow sleeve secured in the hollow portion;
    a first conductor secured in the hollow sleeve, the first conductor comprised of a semiconductor material; and
    an active region in contact with and electrically coupled to an end of the first conductor that extends beyond an end of the hollow sleeve.

2. The analyte sensor of claim 1, further comprising a second conductor secured in the hollow sleeve.

3. The analyte sensor of claim 2, further comprising a third conductor secured in the hollow sleeve.

4. The analyte sensor of claim 3, wherein the third conductor comprises a fill detection electrode.

5. The analyte sensor of claim 1, wherein the first conductor comprises a core of a conductive material and a cladding comprised of the semiconductor material.

6. The analyte sensor of claim 5, wherein the conductive material of the core of the first conductor comprises carbon and the semiconductor material of the cladding comprises silicon carbide.

7. The analyte sensor of claim 1, wherein the active region is included within a cavity formed, at least in part, by the inner wall of the hollow cylindrical member, proximate to a first end of the hollow cylindrical member.

8. The analyte sensor of claim 1, further comprising a coded region.

9. The analyte sensor of claim 1, wherein the sensor is adapted to sense an analyte comprising one or more of glucose, lactate, aspartate, glutamate, and alcohol.

10. The analyte sensor of claim 1, further comprising a fill detector.

11. The analyte sensor of claim 1, further comprising a second conductor secured in the hollow sleeve and surrounding the first conductor.

12. The analyte sensor of claim 1, wherein the hollow cylindrical member includes a first end and an opposing second end, the first end of the hollow cylindrical member including a lancet point, and wherein the first conductor extends out of the second end of the hollow cylindrical member.

13. The analyte sensor of claim 1, wherein the hollow cylindrical member comprises a hollow lancet including the hollow portion and a lancet point at an end thereof.

14. The analyte sensor of claim 1, further comprising:
a cavity defined by the inner wall of the hollow cylindrical member, an end of the hollow cylindrical member, and an end of the hollow sleeve secured therein; and
wherein the active region is positioned within the cavity.

15. The analyte sensor of claim 1, further comprising:
a lancet point formed on an end of the hollow cylindrical member;
a cavity formed within the hollow portion, proximate to an end of the hollow sleeve secured in the hollow portion and proximate to an end of the first conductor; and
wherein the active region is positioned within the cavity.

16. A testing apparatus, comprising:
a port receiving an analyte sensor, wherein the analyte sensor comprises:
a hollow cylindrical member including a hollow portion;
a hollow sleeve secured in the hollow portion;
a first conductor secured in the hollow sleeve, the first conductor comprised of a semiconductor material;
an active region in contact with and electrically coupled to an end of the first conductor that extends beyond an end of the hollow sleeve.

17. The method of manufacturing an analyte sensor, comprising:
providing a first conductor comprised of a semiconductor material;
applying and electrically coupling an active region to an end of the first conductor;
receiving and securing the first conductor in a hollow sleeve, wherein the end of the first conductor extends beyond an end of the hollow sleeve; and
receiving and securing the hollow sleeve in the hollow cylindrical member.

18. An analyte sensor, comprising:
a hollow cylindrical member including a first end and a second end and an inner wall defining a hollow portion extending between the first end and the second end,
the first end of the hollow cylindrical member defining an opening and including a lancet point formed thereon;
a hollow sleeve having a first end secured in the hollow portion proximate the first end of the hollow cylindrical member;
a first conductor and a second conductor secured in the hollow sleeve are electrically insulated from each other, each of the first and second conductors comprising a semiconductor fiber having:
a first end extending beyond the first end of the hollow sleeve proximate the first end of the hollow cylindrical member; and
a second end extending out of the second end of the hollow cylindrical member;
an active region in contact with and electrically coupled to the first ends of the semiconductor fibers of the first and second conductors;
wherein at least one of the second ends of the semiconductor fibers of the first and second conductors includes a coded region.

* * * * *

UNITED STATES PATENT AND TRADEMARK OFFICE
CERTIFICATE OF CORRECTION

PATENT NO. : 9,173,597 B2  Page 1 of 1
APPLICATION NO. : 13/119222
DATED : November 3, 2015
INVENTOR(S) : Swetha Chinnayelka et al.

It is certified that error appears in the above-identified patent and that said Letters Patent is hereby corrected as shown below:

IN THE SPECIFICATION

In Column 5, Line 28, delete "120" and insert -- 120) --, therefor.

In Column 7, Line 19, delete "Pyrolloquinoline" and insert -- Pyrroloquinoline --, therefor.

In Column 12, Line 4, delete "mechanism) not shown)." and insert -- mechanism (not shown). --, therefor.

IN THE CLAIMS

In Column 13, Line 29, in Claim 17, delete "The" and insert -- A --, therefor.

In Column 14, Line 6, in Claim 17, delete "in the" and insert -- in a --, therefor.

In Column 14, Line 25, in Claim 18, delete "member;" and insert -- member; and --, therefor.

In Column 14, Line 28, in Claim 18, delete "conductors;" and insert -- conductors, --, therefor.

Signed and Sealed this
First Day of March, 2016

Michelle K. Lee
*Director of the United States Patent and Trademark Office*